(12) United States Patent
Lee et al.

(10) Patent No.: US 6,746,583 B2
(45) Date of Patent: Jun. 8, 2004

(54) MICROCHIP-BASED CARBON DIOXIDE GAS SENSOR

(75) Inventors: Jae Seon Lee, Seoul (KR); Jae Ho Shin, Seoul (KR); Min Hyung Lee, Kyunggi-do (KR); Hakhyun Nam, Seoul (KR); Geun Sig Cha, Seoul (KR)

(73) Assignee: i-Sens, Inc., Seoul (KR)

( * ) Notice: Subject to any disclaimer, the term of this patent is extended or adjusted under 35 U.S.C. 154(b) by 182 days.

(21) Appl. No.: 09/877,857

(22) Filed: Jun. 8, 2001

(65) Prior Publication Data

US 2002/0011408 A1 Jan. 31, 2002

(30) Foreign Application Priority Data

Jun. 12, 2000 (KR) ........................................ 2000-32050

(51) Int. Cl.[7] ............................................ G01N 27/327
(52) U.S. Cl. .................. 204/403.1; 204/415; 204/435; 204/431
(58) Field of Search ............................ 204/403.1, 415, 204/416, 418, 419, 420, 435, 431

(56) References Cited

U.S. PATENT DOCUMENTS

| 4,473,456 A | * | 9/1984 | Hawkins ................. 204/403.1 |
| 5,183,549 A | * | 2/1993 | Joseph et al. .............. 204/415 |
| 5,326,531 A |   | 7/1994 | Hahn et al. |

OTHER PUBLICATIONS

An article entitled "An Improved potentiometric pCO2 Microelectrode", By Pingsan Zhao et al., Department of Marine Sciences, The University of Georgia, Athens, Georgia 30602, Analytical Chemistry, vol. 69, No. 24, Dec. 15, 1997, pp. 5052–5058.
An article entitled "A Planar pCO2 Sensor With Enhanced Electrochemical Properties", By Jae Ho Shin, Chemical Sensor Research Group, Department of Chemistry, Kwangwoon University, Seoul 139–701, Korea, Analytical Chemitry, vol. 72, No. 18, Sep. 15, 2000, pp. 4468–4473.

* cited by examiner

*Primary Examiner*—Alex Noguerala
(74) *Attorney, Agent, or Firm*—Bachman & LaPointe, P.C.

(57) ABSTRACT

There is provided a microchip-based differential-type carbon dioxide gas sensor for detecting dissolved carbon dioxide levels. It functions with at least one working electrode composed of an unbuffered hydrogel membrane containing a certain amount of sodium bicarbonate and a pH-sensitive gas-permeable membrane; and a reference electrode composed of a buffered hydrogel membrane and a pH-sensitive gas-permeable membrane. The unbuffered hydrogel membrane contains carbonic anhydrase, which reduces the time period for the hydration of carbon dioxide, thereby allowing the quick measurement of the level of carbon dioxide. In addition to being significantly improved in stabilization, sensing, and recovering time periods, the differential-type carbon dioxide gas sensor can be fabricated in small sizes and quickly measure levels of carbon dioxide dissolved in sample solution.

12 Claims, 7 Drawing Sheets

MICROCHIP-BASED CARBON DIOXIDE GAS SENSOR

FIELD OF THE INVENTION

The present invention relates to a miniature, differential-type sensor being able to quickly measure levels of carbon dioxide dissolved in liquid solutions, which functions with a working electrode composed of unbuffered hydrogel and a pH-sensitive gas-permeable membrane, and a reference electrode composed of buffered hydrogel and a pH-sensitive gas-permeable membrane. More particularly, the present invention relates to the introduction of carbonic anhydrase into the unbuffered hydrogel to reduce the hydration time of carbon dioxide, thereby quickly measuring carbon dioxide levels, and the introduction of a controlled content of bicarbonate ions into the unbuffered hydrogel to improve the sensitivity of the sensor.

BACKGROUND OF THE INVENTION

Quantification of carbon dioxide levels can be applied to various fields. For example, it can be applied for analyzing clinical samples in the medical diagnostic fields, for regulating combustion processes in chemical analysis fields, for diagnosing the severity of the green house effect, and for measuring the indexes related to aquatic ecosystem in an environmental field. The exact measurement of dissolved carbon dioxide becomes increasingly significant.

In a human body, carbon dioxide is present in a small quantity as a metabolic end product, resulting mainly from the metabolism of foods. When the partial pressure of carbon dioxide in blood is 40 mmHg or higher, carbon dioxide is released from erythrocytes. The free carbon dioxide is dissolved in blood plasma and hydrated to form carbonic acid ($H_2CO_3$), which is in turn dissociated into hydrogen ion ($H^+$) and bicarbonate ion ($HCO_3^+$). Since the total content of carbon dioxide ($CO_2$ gas, $H_2CO_3$, $HCO_3^-$, $CO_3^{2-}$) in blood plasma affects the acid-base balance and pH of blood, as well as being an index for pulmonary ventilation, alveolar gas exchange capacity, and the quantity of the gas transferred to somatic tissues from blood, it is very important to accurately measure the levels of carbon dioxide dissolved in blood.

Carbon dioxide also plays an important role in the field of the ecosystem. For example, carbon dioxide is in an equilibrium state between air and water. In natural water, bicarbonate ions ($HCO_3^-$) act as a buffering reagent and keep the pH constant. As the concentration of carbon dioxide in the water is closely related to the health of aquatic ecosystems, it is important to accurately measure levels of carbon oxide dissolved in water in order to detect changes of the aquatic ecosystem.

For measuring concentrations of carbon dioxide, two types of carbon dioxide gas sensors are known: a Severinghaus-type carbon dioxide gas sensor, wherein an external reference electrode, a pH-sensitive electrode and a gas-permeable membrane are simultaneously housed in one sensor body; and a differential-type carbon dioxide gas sensor, wherein a working electrode and a reference electrode are separated in different sensor body.

As shown in FIG. 1, the Severinghaus-type carbon dioxide gas sensor comprises an external reference electrode 14, a working electrode 16 with pH-sensitive membrane 11, a gas-permeable membrane 12, and an unbuffered solution 13 in one sensor body 17. When the Severinghaus-type carbon dioxide gas sensor is immersed in a sample solution 18 of interest, a potential is generated by the sensor and displayed on a voltmeter 15.

Such a Severinghaus-type carbon dioxide gas sensor suffers from difficulty in the fabrication and miniaturization of the sensor, because the reference electrode is incorporated inside the sensor. In addition, another disadvantage of Severinghaus-type carbon dioxide gas sensor is that it cannot be used when the level of carbon dioxide is low. That is, at a low level of carbon dioxide, the Severinghaus-type carbon dioxide sensor is so slow in sensing rate and recovery rate that it cannot be used in automatic gas sensing systems. Furthermore, Severinghaus-type carbon dioxide gas sensor suffers from the disadvantage of being poor in detection limit.

FIG. 2 illustrats a differential-type carbon dioxide gas sensor, characterized in that a working electrode is separated from a reference electrode. The differential-type carbon dioxide gas sensor comprises a working electrode 20 composed of an unbuffered inner reference solution 13 and a pH-sensitive gas-permeable membrane 19; and a reference electrode 21 composed of a buffered inner reference solution 22 and the same pH-sensitive gas-permeable membrane 19 as that in a working electrode.

In the differential-type carbon dioxide gas sensor, charge separation and the accompanying potential difference occur at 4 different sites: $E_{outer1}$ between the pH-sensitive gas-permeable membrane 19 of the working electrode 20 and the sample solution 18; $E_{outer2}$ between the pH-sensitive gas-permeable membrane 19 of the reference electrode 21 and the sample solution 18; $E_{inner1}$ between the pH-sensitive gas-permeable membrane 19 of the working electrode 20 and the unbuffered inner reference solution 13; and $E_{inner2}$ between the pH-sensitive gas-permeable membrane 19 of the reference electrode 21 and the buffered inner reference solution 22. When such charge separations occur, $E_{outer1}$ and $E_{outer2}$ have the same value and thus can be counterbalanced, as the same pH-sensitive gas-permeable membranes are used. On the other hand, the charge separation $E_{inner2}$ between the pH-sensitive gas-permeable membrane 19 of the reference electrode 21 and the buffered inner reference solution 22 is maintained at a constant value as the reference solution is buffered. Therefore, a change in carbon dioxide levels in a sample solution 18 causes only the charge separation $E_{inner1}$ between the pH-sensitive gas-permeable membrane 19 and the unbuffered inner reference solution 13 of the working electrode 20, so that the resulting potential change enables the carbon dioxide levels of the sample solution to be quantitatively detected.

However, the conventional differential-type carbon dioxide gas sensor also suffers from long period of response time for sensing and recovery at a low level of carbon dioxide. Also, its detection limits are still not satisfactory. However, the differential-type carbon dioxide gas sensors are easier to miniaturize than the Severinghaus-type one.

Microchip-based carbon dioxide gas sensor may be fabricated in small sizes since all parts thereof including electrolyte layers can be fabricated as a layered structure. It can be also used as a multi-sensor capable of detecting various ions and gas species simultaneously with one chip. Additionally, the mass production of the microchip-based sensor can be achieved, resulting in reduced production cost. Furthermore, the small size of its sensing site makes it possible to detect even a trace amount of samples.

SUMMARY OF THE INVENTION

In this invention, we combined two advanced technologies in an attempt to obtain a planar microchip-based carbon dioxide sensing device with faster-preconditioning and response characteristics for being dissolved carbon dioxide measurement in physiological samples: one is a differential sensing arrangement to facilitate the micro-fabrication of potentiometric carbon dioxide electrodes, and the other is the use of carbonic anhydrase to shorten total measurement time. The pH-sensitive polymeric membranes adapted for use in constructing a differential carbon dioxide sensor system in this work function as both a gas-permeable membrane and an internal pH-sensing element. In the differential configuration, the carbon dioxide electrode is made with an unbuffered recipient layer including carbonic anhydrase, hence the pH changes are promoted and detected. The reference electrode, on the other hand, employs a strongly buffered hydrogel layer; therefore diffused carbon dioxide cannot change the pH in the recipient layer. In addition, the pH and ion response signals of the outer membrane surfaces (on the sample side) at both the carbon dioxide and the reference electrodes are identical, therefore they cancel out.

Therefore, it is an object of the present invention to provide a miniaturized differential-type carbon dioxide gas sensor comprising all parts of the sensor including electrolyte layers fabricated as a dried layered structure, such that it can be miniaturized.

Another object of the present invention is to provide a composition of unbuffered hydrogel membrane of the differential-type carbon dioxide gas sensor.

The above objects and other objects described in the detailed description of the present invention could be accomplished by the provision of a differential-type carbon dioxide gas sensor, comprising:

a) a working electrode composed of unbuffered hydrogel and pH-sensitive gas-permeable membrane, wherein carbonic anhydrase is incorporated into a unbuffered hydrogel; and, b) a reference electrode composed of buffered hydrogel and pH-sensitive gas-permeable membrane.

The present invention also provides a composition of unbuffered hydrogel of a working electrode, which comprises: sodium bicarbonate; sodium chloride (or potassium chloride); and hygroscopic hydrogel and carbonic anhydrase.

BRIEF DESCRIPTION OF THE DRAWINGS

FIG. 8b is an assay graph for the plot of FIG. 8a.

Figure 1:
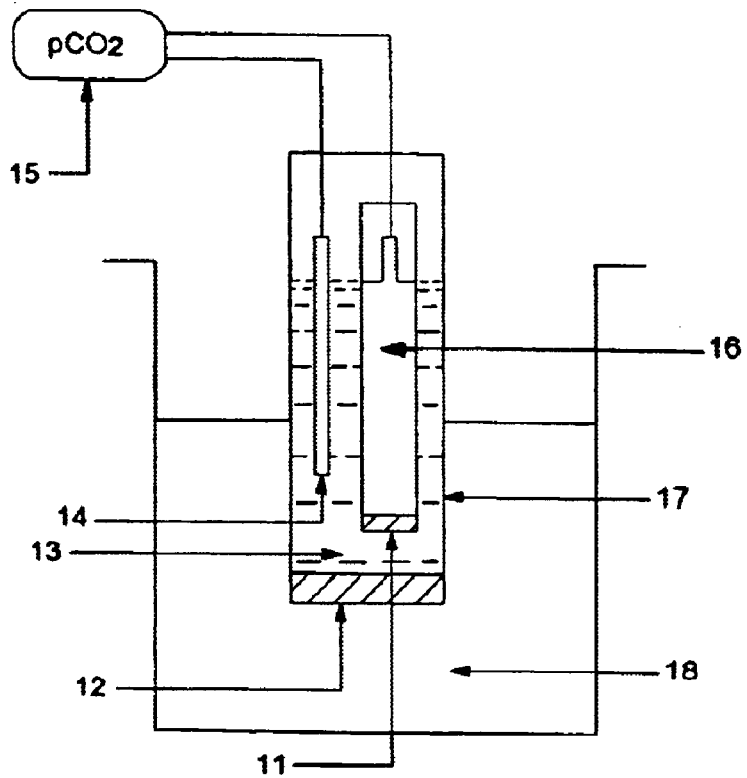
FIG. 1 is a schematic view showing the structure of the conventional Severinghaus-type $pCO_2$ gas sensor.
Figure 2:
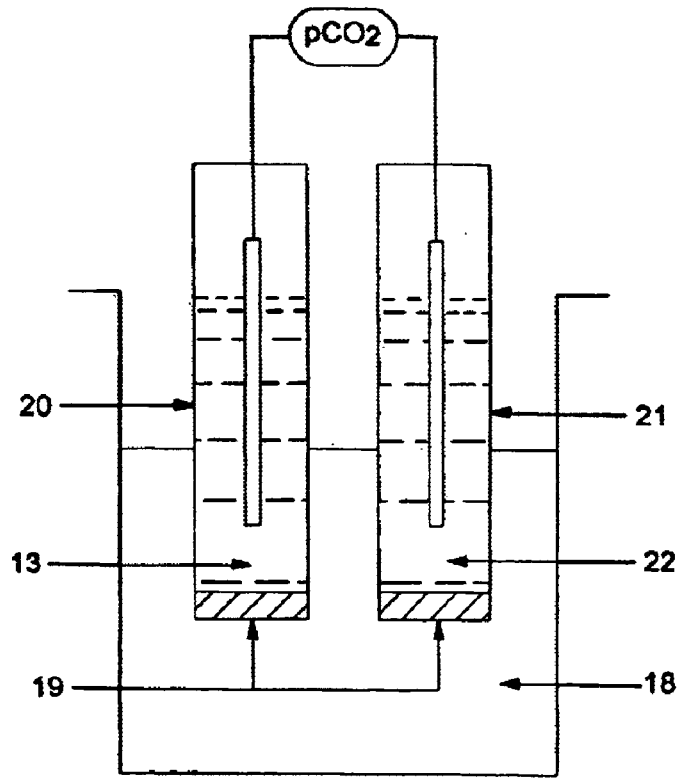
FIG. 2 is a schematic view showing the structure of a conventional differential-type $pCO_2$ gas sensor.

11: pH-sensitive membrane
12: gas-permeable membrane
13: unbuffered inner reference solution
14: external reference electrode
15: voltmeter
16: internal reference electrode
17: sensor body
18: sample solution
19: pH-sensitive gas-permeable membrane
20: working electrode
21: reference electrode
22: buffered inner reference solution
23: electrode layer
24: insulating film
25: unbuffered hydrogel membrane
26: buffered hydrogel membrane
27: alumina substrate

DETAILED DESCRIPTION OF THE INVENTION

The application of the preferred embodiments of the present invention is best understood with reference to the accompanying drawings, wherein like reference numerals are used for like and corresponding parts, respectively.

In one aspect, there is provided a microchip-based differential-type carbon dioxide gas sensor in which concepts for a differential-type gas sensor and a microchip-based gas sensor are applied in combination. The microchip-based differential-type carbon dioxide gas sensor comprises:

a) a working electrode composed of unbuffered hydrogel and pH-sensitive gas-permeable membrane, wherein carbonic anhydrase is incorporated into a unbuffered hydrogel; and, b) a reference electrode composed of buffered hydrogel and pH-sensitive gas-permeable membrane.

In the microchip-based carbon dioxide gas sensor of the present invention, inner solutions used in the working electrode and the reference electrode are mixed with hydrogel. In addition, carbonic anhydrase that catalyzes hydration of carbonic acid is incorporated into the hydrogel of the working electrode, such that the sensor can quickly sense the change of the levels of carbon dioxide dissoloved in the sample solution. To improve the sensitivity of the sensor, it is preferable to further incorporate a controlled amount of bicarbonate ions into the unbuffered hydrogel.

Figure 3A:
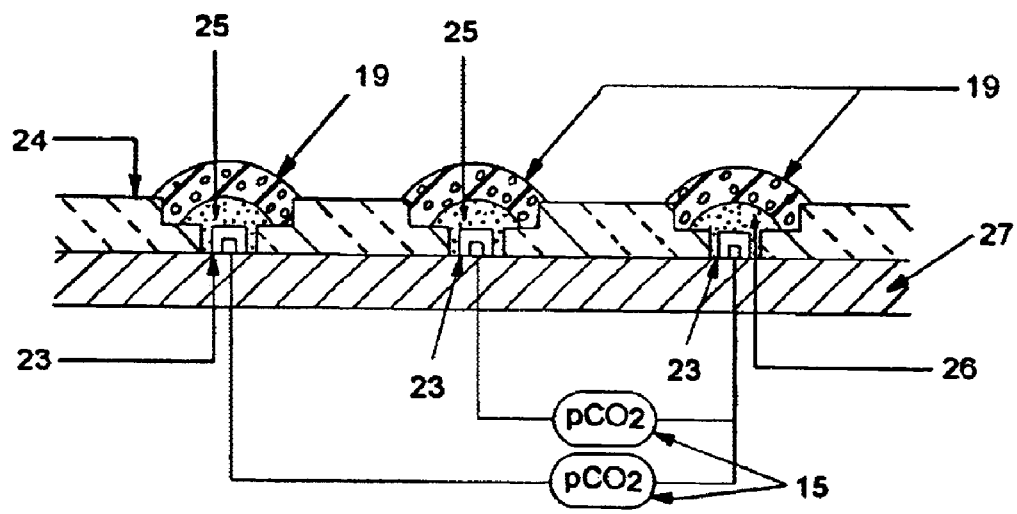
FIG. 3a is a schematic view showing the structure of the differential-type planar $pCO_2$ gas sensor of the present invention, comprising: an alumina substrate 27; voltmeter 15; Ag/AgCl as electrode layer 23; an insulating film 24; an unbuffered hydrogel membrane 25; an buffered hydrogel membrane 26; and pH-sensitive gas-permeable membranes 19, wherein the pH value of unbuffered hydrogel can be varied in accordance with the concentration of carbon dioxide dissolved in sample solution, but the pH value of buffered hydrogel remains constant.

Referring to FIG. 3a, there is provided a microchip-based planar differential-type carbon dioxide gas sensor as one example of the present invention. As shown in FIG. 3a, a set of electrodes 23, composed of Ag/AgCl, is arranged at a regularly spaced interval on an alumina substrate 27 while an insulating film 24 is deposited over the entire alumina substrate 27, except for the areas for the electrode layers 23. The pH-sensitive gas-permeable membranes 19 are placed on the top of each electrode 23 after depositing an unbuffered hydrogel membrane 25 or a buffered hydrogel membrane 26. Preferably, the unbuffered hydrogel membranes 25 contain carbonic anhydrase.

In the present invention, the substrate is selected from the group of alumina, ceramic, silicon, and plastic material, more preferably is used alumina one.

For the miniaturization of a sensor, as mentioned previously, all parts, including electrolyte layers, to be introduced into the sensor, are preferably fabricated as a layered structure. Such a structure leads to the development of multi-sensors that are able to detect various ion and gas species with single chip. In addition, the layered structure is advantageous in mass production, thereby significantly reducing the production cost. In this layered structure, a sensing part responsible for detecting a species of interest can be formed in such a small size that quantitative analysis for carbon dioxide can be achieved even with a very small quantity (10~20 $\mu l$) of a sample.

In the present invention, layered-phase hygroscopic hydrogel is used as inner reference electrolytes of the electrodes. The material suitable for use in the hygroscopic hydrogel is preferably selected from the group consisting of hydroxyethyl cellulose, poly(vinyl alcohol), Methocel, (hydroxypropyl)methyl cellulose, polyacrylic acid, polyvinylpyrrolidone, poly(methylmethacrylate), agar and gelatin.

To increase the sensitivity to the change of carbon dioxide levels and to shorten the period required to return to its initial state, the unbuffered hydrogel membrane 25 comprises carbonic anhydrase in accordance with the present invention. In detail, the unbuffered hydrogel membrane 25 comprises a hydrogel consisting essentially of $2.4 \times 10^{-2} \sim 8.1 \times 10^{-2}$% by weight (3~10 mM) of sodium bicarbonate, $5.6 \times 10^{-4} \sim 5.6 \times 10^{-3}$% by weight (0.1~1.0 mM) of sodium chloride or potassium chloride and 1~4% by weight of a hygroscopic material, and 1.0~6.0 mg of carbonic anhydrase.

More particularly, the carbonic anhydrase incorporated into the unbuffered hydrogel membrane 25 functions to promote the hydration of carbon dioxide, enabling the sensor to respond 2~3 times faster to the change in carbon dioxide levels than the sensors which employ no carbonic anhydrase. However, the sensor does not shorten the response time proportional to the quantity of the carbonic anhydrase introduced. Thus, preferable amount of carbonic anhydrase used is in the range of 0.1~6.0 mg per 1 ml of the hydrogel.

When the bicarbonate ion is incorporated in the range of from 0.5 to 2.0 mM into the unbuffered hydrogel membrane 25 of the working electrode, the carbon dioxide gas sensor quickly responds to the carbon dioxide, but is poor in sensitivity. On the other hand, when the bicarbonate ion is used in the range of from 5.0 mM to 10.0 mM, the carbon dioxide gas sensor exhibits high sensitivity, but at the cost of a slightly prolonged response time. Accordingly, it is preferred that bicarbonate ions are introduced at an amount of 3~10 mM in order for the carbon dioxide gas sensor to respond within a reasonably short period of time with high sensitivity.

Preferably, the buffered hydrogel membrane 26 can be prepared by dissolving 1~5 mM of sodium chloride (or potassium chloride) and 1~4% by weight of a hygroscopic material in an acidic buffer solution of pH 5.0~5.7. The acidic buffer can be selected from the group consisting of HOMOPIPES (homopiperazine-N,N'-bis-2-(ethane sulfonic acid)), MES (2-(N-morpholino)ethanesulfonic acid), and BIS-TRIS (bis-(2-hydroxyethyl)imino-tris(hydroxymethyl) methane).

In the microchip-based differential-type carbon dioxide gas sensor of the present invention, carbon dioxide passes through the pH-sensitive gas-permeable membrane and is hydrated in the unbuffered hydrogel membrane to generate hydrogen ions ($H^+$). Quantification of the carbon dioxide is obtained by measuring the hydrogen ions. Therefore, the performance of the carbon dioxide gas sensor is also dependent upon the kind of the pH-sensitive gas-permeable membrane used. Preferable pH-sensitive gas-permeable membrane has an excellent pH sensitivity and suitable adhesiveness for fabricating a carbon dioxide gas sensor in a planar form.

The pH-sensitive gas-permeable membrane for use in the carbon dioxide gas sensor is composed mainly of a polymer matrix, a hydrogen ion-selective material, a plasticizer, and a lipophilic additive.

As a matrix, PVC (polyvinyl chloride), PU (polyurethane) and silicone rubber, which have the suitable adhesiveness and excellent biocompatibility adaptable to medical blood analyzers, are preferably used alone or in combination. The amount used is in the range of 32~45% by weight based on the total weight of the membrane.

As the hydrogen ion-selective material is selected from the group consisting of TDDA (tridodecyl amine), 4-nonadecylpyridine, N,N-dioctadecylmethylamine, and octadecyl isonicotinate, TDDA (tridodecyl amine) is preferable, but not limited thereto. The amount used is in the range of 1.0~4.5% by weight.

The plasticizer may be DOS (bis(2-ethylhexyl)sebacate) or NPOE (2-nitrophenyl octyl ether) and be preferably used at an amount of 50~66% by weight.

KTpClPB (potassium tetrakis [4-chlorophenyl]borate) is an useful lipophilic additive and preferably is added at an amount of 0.9~1.5% by weight.

Further to these, addition of N-[3-(trimethoxysilyl) propyl]ethylene diamine to the pH-sensitive gas-permeable membrane composition is greatly helpful in improving the adhesiveness of the membrane while maintaining its electrochemical properties.

Also, in another aspect of the present invention, there is provided a method for preparing planar format differential-type carbon dioxide gas sensor, comprising:

a) forming unbuffered and buffered hydrogel layers onto a working electrode and a reference electrode of the planar sensor by adding the unbuffered hydrogeled solution dropwise onto a working electrode and buffered hydrogel solution onto a reference electrode respectively, followed by drying the unbuffered and the buffered hydrogels;

b) forming a pH-sensitive gas-permeable membrane layer by adding the solution containing pH-sensitive gas-permeable materials dropwise onto the dried hydrogel layers, followed by drying.

According to the embodiment of the invention, the microchip-based differential-type carbon dioxide gas sensor comprising buffered and unbuffered hydrogel membranes and pH-sensitive gas-permeable membranes in accordance with the present invention was found to quickly respond to the change of carbon dioxide levels dissolved in samples containing various electrolyte ion species ($Ca^{2+}$, $Na^+$, $K^+$, and $H^+$) and gases ($O_2$ and $CO_2$) with high sensitivity, and return to the initial state within a short period of time as measured by flow injection analysis. In addition, the sensing parts responsible for the detection of species of interest in the carbon dioxide gas sensor is small enough to allow accurate measurement of carbon dioxide levels even with a small quantity (10~20 μl) of samples.

In a further aspect, there is provided a multi-sensor comprising a reference electrode composed of a buffered hydrogel membrane and a working electrode composed of an unbuffered hydrogel membrane.

Figure 3B:
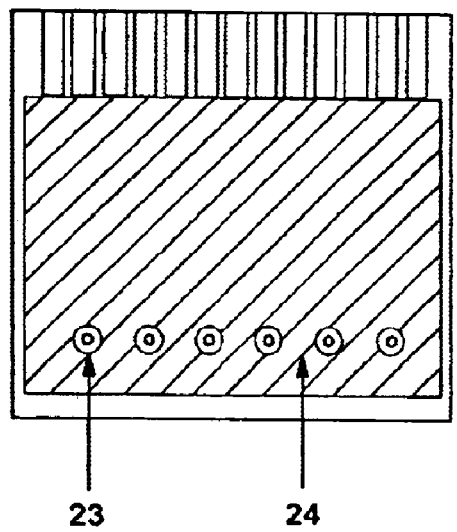
FIG. 3b is a front view of the sensor chip used to demonstrate the utility of present invention.

A description is given of the multi-sensor in conjunction with FIG. 3b. As shown in the front view of FIG. 3b, the multi-sensor of the present invention is of a planar type having a structure in which one reference electrode and several working electrodes are provided on one chip and, hence, various ion and gas species can be detected simultaneously. Additionally, the buffered and unbuffered hydrogel membranes introduced into the reference electrode and the working electrode significantly reduce the size of the carbon dioxide gas sensor.

A better understanding of the present invention may be obtained in the light of the following examples which are set forth to illustrate, but are not to be construed to limit the present invention.

PREPARATION EXAMPLE 1

Preparation of pH-Sensitive Gas-Permeable Membrane 1

In tetrahydrofuran 450 μl, PVC (poly(vinyl chloride)) was dissolved at an amount of 32.1 mg as a matrix, TDDA (tridodecyl amine) at an amount of 2.9 mg as a hydrogen-selective material, DOS (bis(2-ethylhexyl) sebacate) at an amount of 63.6 mg as a plasticizer, and KTpClPB (potassium tetrakis [4-chlorophenyl]borate) at an amount of 1.4 mg as a lipophilic additive, after which the resulting solution was dried at room temperature for 1~2 days to prepare a pH-sensitive gas-permeable membrane.

PREPARATION EXAMPLE 2

Preparation of pH-Sensitive Gas-Permeable Membrane 2

In tetrahydrofuran 450 μl, PU (polyurethane) 32.1 mg, TDDA 2.9 mg, DOS 63.6 mg and KTpClPB 1.4 mg were dissolved, followed by drying the resulting solution at room temperature for 1~2 days to prepare a pH-sensitive gas-permeable membrane.

PREPARATION EXAMPLE 3

Preparation of pH-Sensitive Gas-Permeable Membrane 3

In tetrahydrofuran 450 μl, PVC (polyvinyl chloride) 8.0 mg, PU 24.1 mg, TDDA 2.9 mg, DOS 63.6 mg and KTpClPB 1.4 mg were dissolved, followed by drying the resulting solution at room temperature for 1~2 days to afford a pH-sensitive gas-permeable membrane.

PREPARATION EXAMPLE 4

Preparation of pH-Sensitive Gas-Permeable Membrane 4

In tetrahydrofuran 450 μl, PVC 11.1 mg, PU 33.4 mg, TDDA 4.1 mg, NPOE (2-nitrophenyl octyl ether) 50.5 mg and KTpClPB 0.9 mg were dissolved, followed by drying the resulting solution at room temperature for 1~2 days to prepare a pH-sensitive gas-permeable membrane.

PREPARATION EXAMPLE 5

Preparation of pH-Sensitive Gas-Permeable Membrane 5

In tetrahydrofuran 450 μl, dissolved were the composition of Preparation Example 4 supplemented with N-[3-(trimethoxysilyl)propyl]ethylene diamine 1.0 mg with the aim of greatly improving the adhesiveness of the electrode membrane while maintaining its electrochemical properties, after which the solution was dried at room temperature for 1~2 days to prepare a pH-sensitive gas-permeable membrane.

Compositions for Polymeric, pH-sensitive gas-permeable membranes of Preparation Examples 1 to 4 are summarized in Table 1, below.

TABLE 1

Compositions of Polymeric, pH-Sensitive Gas-Permeable Membranes

| | Matrix | | | $H^+$ ion-selective material | Plasticizer | | Lipophilic additive |
|---|---|---|---|---|---|---|---|
| Example | $PVC^a$ | $PU^b$ | PVC + PU | $TDDA^c$ | $DOS^d$ | $NPOE^e$ | $KT_pClPB^f$ |
| 1 | 32.1 | | | 2.9 | 63.6 | | 1.4 |
| 2 | | 32.1 | | 2.9 | 63.6 | | 1.4 |
| 3 | | | 32.1 | 2.9 | 63.6 | | 1.4 |
| 4 | | | 44.5 | 4.1 | | 50.5 | 0.9 |

Unit: weight %
$^a$poly(vinyl chloride)
$^b$polyurethane
$^c$tridodecyl amine
$^d$bis(2-ethylhexyl) sebacate
$^e$2-nitrophenyl octyl ether
$^f$potassium tetrakis[4-chlorophenyl] borate An examination was made for the sensitivity of pH-sensitive gas-permeable membranes prepared in Preparation Examples 1 to 5. To this end, each of the pH-sensitive gas-permeable membranes was mounted onto an electrode (Phillips, IS-561), and then measured for sensitivity with the aid of a pH meter while titrating a common buffer (10 mM $NaH_2PO_4$/6.7 mM citric acid/11.4 mM boric acid) with a NaOH solution.

The measurement results are given in Table 2, below.

TABLE 2

Sensitivity of pH-Sensitive Gas-Permeable Membrane

| Example | Slope (mV/pH) | Linearity |
|---|---|---|
| 1 | −55.8 | 0.9999 |
| 2 | −55.2 | 0.9999 |
| 3 | −55.2 | 0.9999 |
| 4 | −57.4 | 0.9999 |
| 5 | −56.8 | 0.9999 |

As apparent from Table 2, all pH-sensitive gas-permeable membranes prepared in Preparation Examples 1~5 exhibited excellent sensitivity, among which the best was the pH-sensitive gas-permeable membrane of Preparation Example 4 in which NOPE was used, instead of DOS, as a plasticizer. Accordingly, the pH-sensitive gas-permeable membrane of Preparation Example 4 was used henceforth.

EXAMPLE 1
Preparation of Differential-Type Carbon Dioxide Gas Sensor 1

On an alumina substrate, a homogeneous mixture of 5~10 mg of platinum and 90~95 mg of silver was screen-printed to form metal layers. Subsequently, an inexpensive, highly insulating film was introduced onto the alumina substrate through a screen-printing method. The layered electrodes were immersed in a 1 M $FeCl_3$ solution for 2 min to form layers of AgCl, a sparingly soluble metal salt, thereon. In an aqueous solution containing $4.0\times10^{-2}$% by weight (5.0 mM) of sodium bicarbonate and $2.8\times10^{-3}$% by weight (0.5 mM) of sodium chloride (or potassium chloride), poly(vinyl alcohol) was dissolved at an amount of 4% by weight to make hydrogel. To 350 μl of the hydrogen, 0.1 mg (0.28 mg/ml) of carbonic anhydrase was added, and the resulting unbuffered hydrogel was loaded on the working electrode. Separately, buffered hydrogel was prepared by dissolving poly(vinyl alcohol) at an amount of 4% by weight in an acidic buffer (0.2 M 2-(N-morpholino)ethylanesulfonic acid (MES)-NaOH, pH 5.5) containing 2 mM potassium chloride, loaded on a reference electrode, and dried for 4 min to give an electrolyte layer for planar electrode. On the layered hydrogel membrane thus obtained, a solution of the pH-sensitive gas-permeable membrane of Preparation Example 4 in tetrahydrofuran was added dropwise, followed by drying at room temperature for 2 days to prepare a differential-type carbon dioxide gas sensor.

EXAMPLE 2
Preparation of Differential-Type Carbon Dioxide Gas Sensor 2

A differential-type carbon dioxide gas sensor was prepared in a manner similar to that of Example 1, except that 0.5 mg of carbonic anhydrase was added to 350 μl of the unbuffered hydrogel of Example 1 (carbonic anhydrase 1.40 mg/unbuffered hydrogel 1 ml) to obtain an unbuffered hydrogel membrane.

EXAMPLE 3
Preparation of Differential-Type Carbon Dioxide Gas Sensor 3

A differential-type carbon dioxide gas sensor was prepared in a manner similar to that of Example 1, except that 1.0 mg of carbonic anhydrase was added to 350 μl of the unbuffered hydrogel of Example 1 (carbonic anhydrase 2.80 mg/unbuffered hydrogel 1 ml) to obtain an unbuffered hydrogel membrane.

EXAMPLE 4
Preparation of Differential-Type Carbon Dioxide Gas Sensor 4

A differential-type carbon dioxide gas sensor was prepared in a manner similar to that of Example 1, except that 2.0 mg of carbonic anhydrase was added to 350 μl of the unbuffered hydrogel of Example 1 (carbonic anhydrase 5.60 mg/unbuffered hydrogel 1 ml) to obtain an unbuffered hydrogel membrane.

EXAMPLE 5
Preparation of Differential-Type Carbon Dioxide Gas Sensor 5

The same procedure as in Example 1 was conducted to prepare a differential-type carbon dioxide gas sensor, except that a 0.5 mM sodium bicarbonate solution was used instead of the 5.0 mM sodium bicarbonate solution.

EXAMPLE 6
Preparation of Differential-Type Carbon Dioxide Gas Sensor 6

The same procedure as in Example 1 was conducted to prepare a differential-type carbon dioxide gas sensor, except that a 2.0 mM sodium bicarbonate solution was used instead of the 5.0 mM sodium bicarbonate solution.

EXAMPLE 7
Preparation of Differential-Type Carbon Dioxide Gas Sensor 7

The same procedure as in Example 1 was conducted to prepare a differential-type carbon dioxide gas sensor, except that a 7.0 mM sodium bicarbonate solution was used instead of the 5.0 mM sodium bicarbonate solution.

EXAMPLE 8
Preparation of Differential-Type Carbon Dioxide Gas Sensor 8

The same procedure as in Example 1 was conducted to prepare a differential-type carbon dioxide gas sensor, except that a 10.0 mM sodium bicarbonate solution was used instead of the 5.0 mM sodium bicarbonate solution.

EXAMPLE 9
Preparation of Differential-Type Carbon Dioxide Gas Sensor 9

Following the same procedure as in Example 1, except for using a 15.0 mM sodium bicarbonate solution instead of the 5.0 mM sodium bicarbonate, a differential-type carbon dioxide gas sensor was prepared.

EXAMPLE 10
Preparation of Differential-Type Carbon Dioxide Gas Sensor 10

Using the pH-sensitive gas-permeable membrane prepared in Preparation Example 5, a differential-type carbon dioxide gas sensor was prepared in a manner similar to that of Example 1.

EXPERIMENTAL EXAMPLE 1
Sensitivity of Carbon Dioxide Gas Sensor According to Introduction of Carbonic Anhydrase An examination was made of the influence of carbonic anhydrase on the sensitivity and recovery time of the carbon dioxide gas sensor.

Figure 4:
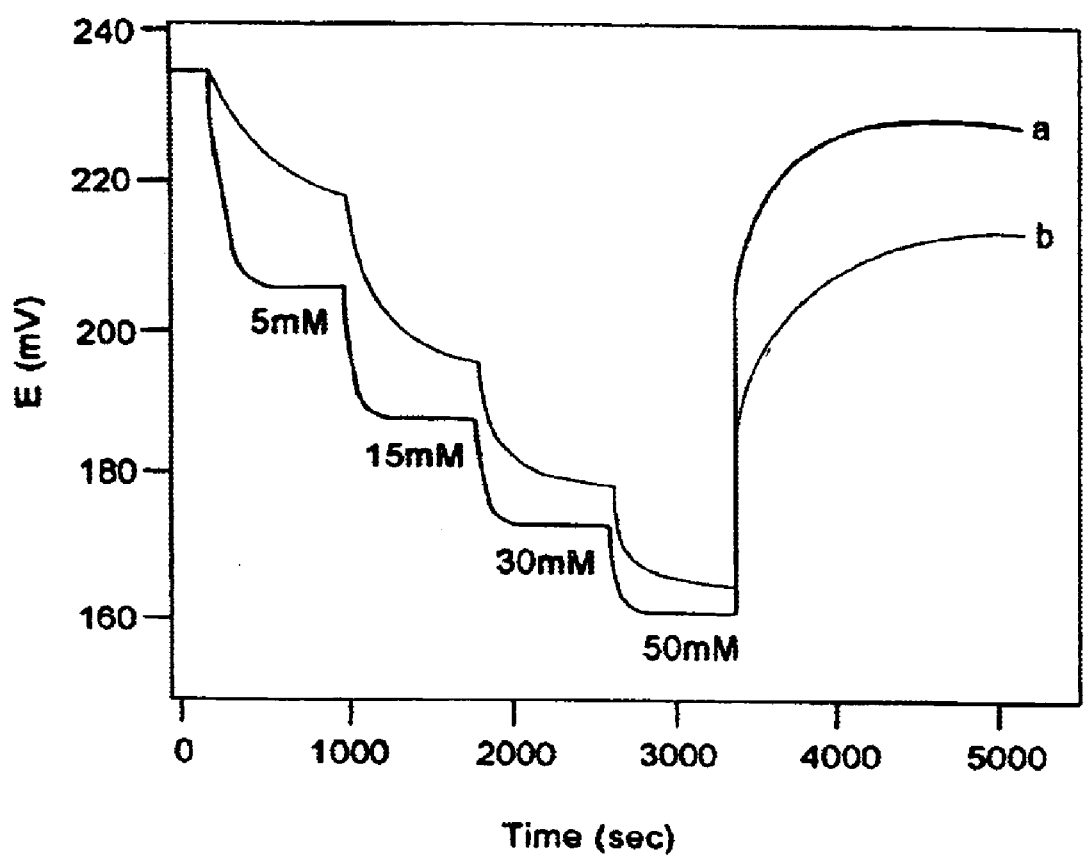
FIG. 4 shows the dynamic response curves of the carbon dioxide sensor to the change in the total concentration of carbon dioxide dissolved in sample solution, (a) the $pCO_2$ sensor of Example 4 into which carbonic anhydrase is introduced at an amount of 5.60 mg per ml of the unbuffered hydrogel; and (b) a control $pCO_2$ sensor into which no carbonic anhydrase is introduced.

Through the addition of 0.3 M Tris buffer (tris (hydroxymethyl)aminomethane) adjusted to pH 7.4 with HCl, a standard solution of 1 M $NaHCO_3$ was changed in total dissolved carbon dioxide level stepwise to 5 mM, 15 mM, 30 mM and 50 mM, and from this level to the initial state. During the modulation of the carbon dioxide level, the differential-type carbon dioxide gas sensor of Example 4 was used to measure the potential change and response time, along with a control sensor, which was deficient in carbonic anhydrase. The measurements are shown in FIG. 4 and Table 3, below. In FIG. 4, potential differences detected by the differential-type carbon dioxide gas sensor of Example 4 (a) and the control sensor (b) were plotted against the time period that it takes to sense 95% of the carbon dioxide levels.

TABLE 3

Response Time of a Carbon Dioxide Gas sensor

| Carbon dioxide level in sample solution | | Response time (sec)[a] | |
|---|---|---|---|
| | | a | b |
| Initial state | → 5 mM | 220 | 695 |
| 5 mM | → 15 mM | 215 | 660 |
| 15 mM | → 30 mM | 205 | 520 |
| 30 mM | → 50 mM | 260 | 565 |
| 50 mM | → initial state | 525 | 915 |

[a] period time to sense 95% of the carbon dioxide levels

As demonstrated in Table 3 and FIG. 3, the carbon dioxide gas sensor into which carbonic anhydrase was introduced (a) responded faster by a factor of 2 or 3 than the carbon dioxide gas sensor into which no carbonic anhydrase was introduced (b). Particularly when the carbon dioxide level changed from the initial value to as low as 15 mM, the carbonic anhydrase-based sensor exhibited three times faster response and twice shorter recovery times than the control sensor deficient of carbonic anhydrase.

EXPERIMENTAL EXAMPLE 2

Sensitivity of Carbon Dioxide Gas Sensor According to the Content of Carbonic Anhydrase in Unbuffered Hydrogel Membrane An examination was made to determine how the differential-type carbon dioxide sensor behaves in terms of sensitivity according to the level of carbonic anhydrase in the unbuffered hydrogel membrane.

In this regard, the carbon dioxide gas sensors of Example 1 (carbonic anhydrase 0.28 mg/unbuffered hydrogel 1 ml), Example 2 (carbonic anhydrase 1.40 mg/unbuffered hydrogel 1 ml), Example 3 (carbonic anhydrase 2.80 mg/unbuffered hydrogel 1 ml) and Example 4 (carbonic anhydrase 5.60 mg/ unbuffered hydrogel 1 ml) were examined, along with a control carbon dioxide gas sensor (no carbonic anhydrase introduced), to measure their potential change and response time over the carbon dioxide concentration range of 5~50 mM in the same manner as in Example 1. The results are shown in FIGS. 5a and 5b.

Figure 5A:
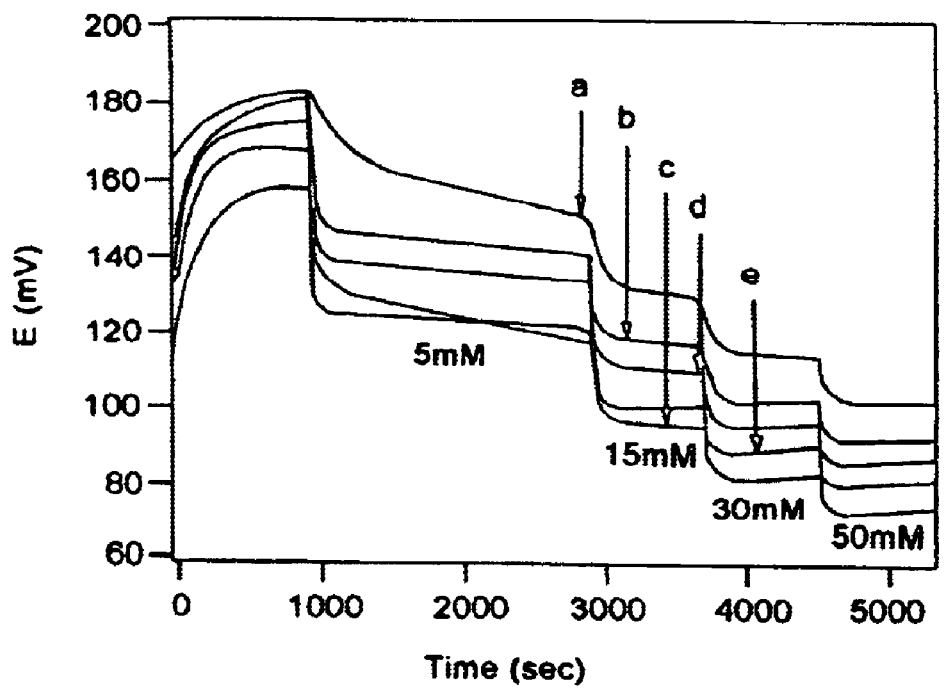
FIG. 5a is a set of dynamic response curves of various carbon dioxide sensors to the change in total dissolved carbon dioxide level in sample solution, in which the sensors have different amount of carbonic anhydrase is introduced into the unbuffered hydrogel membrane of a working electrode: (a) a control $pCO_2$ sensor with no carbonic anhydrase; (b) the $pCO_2$ sensor of Example 1 with 0.28 mg per ml of carbonic anhydrase; (c) the $pCO_2$ sensor of Example 2 with 1.40 mg per ml of carbonic anhydrase; (d) the $pCO_2$ sensor of Example 3 with 2.80 mg per ml of carbonic anhydrase; and (e) the $pCO_2$ sensor of Example 4 with 5.60 mg per ml of carbonic anhydrase.
Figure 5B:
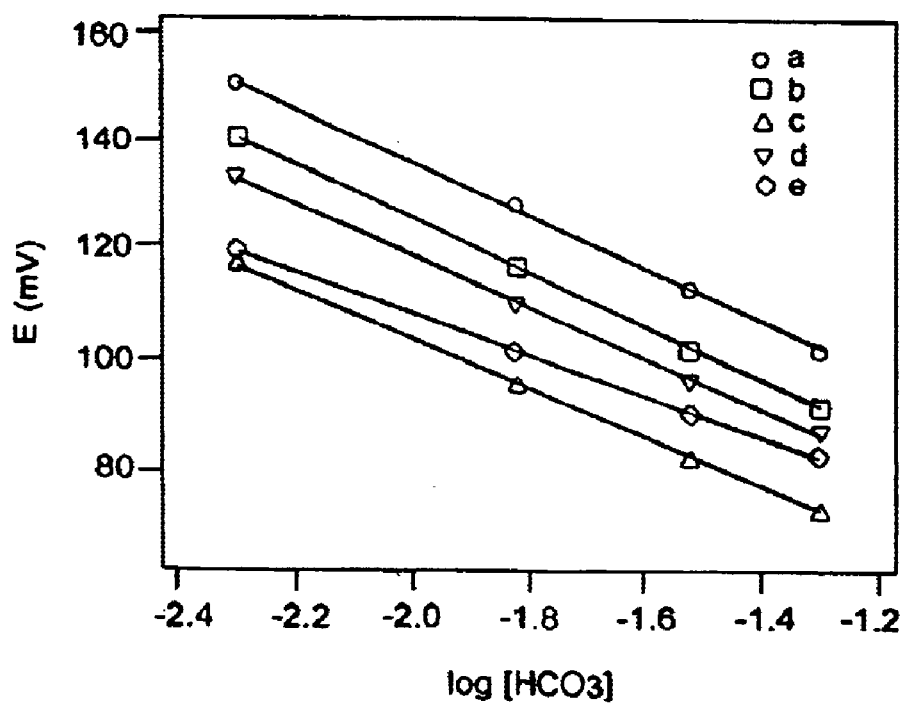
FIG. 5b is calibration curves for the plots of FIG. 5a showing the sensitivity to carbon dioxide.

Over the sensor deficient in carbonic anhydrase (a), as shown in FIGS. 5a and 5b, the sensors into which carbonic anhydrase was introduced at amounts of 0.28 mg (b), 1.40 mg (c), 2.80 mg (d) and 5.60 mg (d) per ml of unbuffered hydrogel, are far superior in response time. However, the sensors do not exhibit sensitivity in proportion to the quantity of carbonic anhydrase. When both response time and sensitivity are taken into consideration, the most preferable amount of carbonic anhydrase was 0.28 mg (b) or 1.40 mg (c) per ml of unbuffered hydrogel.

EXPERIMENTAL EXAMPLE 3

Electrochemical Properties of Carbon Dioxide Gas Sensor According to Bicarbonate Ion Level in Unbuffered Hydrogel Membrane An examination was made to determine how the differential-type carbon dioxide sensor behaves in terms of sensitivity according to the level of bicarbonate ions in the unbuffered hydrogel membrane.

In this regard, the carbon dioxide gas sensors prepared in Example 1 (0.5 mM bicarbonate ion), Example 5 (2.0 mM bicarbonate ion), Example 6 (5.0 mM bicarbonate ion), Example 7 (7.0 mM bicarbonate ion), Example 8 (10 mM bicarbonate ion), and Example 9 (15.0 mM bicarbonate ion) were examined to measure their potential change and response time over the carbon dioxide concentration range of 5~50 mM in the same manner as in Example 1. The results are given in Table 4, below and shown in FIGS. 6a and 6b.

TABLE 4

Electrochemical Properties of Carbon Dioxide Gas Sensor According to Level of Bicarbonate Ions

| Carbon dioxide gas sensor | Example | Bicarbonate ion (mM) | Slope (mV/dec.) | Linearity |
|---|---|---|---|---|
| a | 5 | 0.5 | −35.2 | 0.999 |
| b | 6 | 2.0 | −40.5 | 0.999 |
| c | 1 | 5.0 | −50.7 | 0.999 |
| d | 7 | 7.0 | −48.4 | 0.998 |
| e | 8 | 10.0 | −48.3 | 0.998 |
| f | 9 | 15.0 | −41.7 | 0.997 |

Figure 6A:
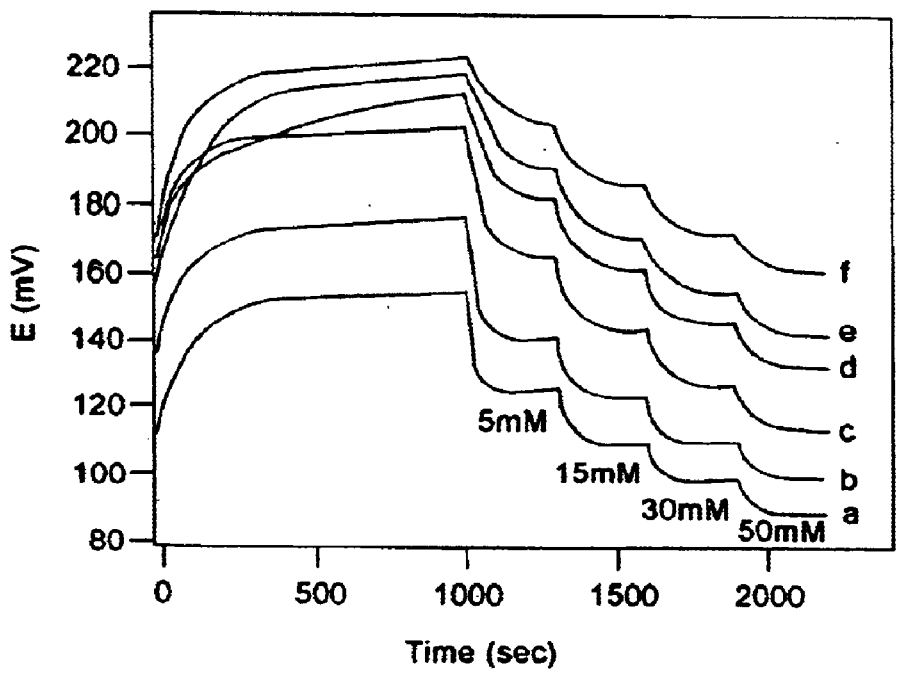
FIG. 6a is dynamic response curves in which, with regard to change in the total dissolved carbon dioxide level in a sample solution, in which the sensors have different amount of sodium bicarbonate is introduced into the unbuffered hydrogel membrane of working electrode: (a) the $pCO_2$ sensor of Example 5 with 0.5 mM bicarbonate ions; (b) the $pCO_2$ sensor of Example 6 with 2.0 mM bicarbonate ions; (c) the $pCO_2$ sensor of Example 1 with 5.0 mM bicarbonate ions; (d) the $pCO_2$ sensor of Example 7 with 7.0 mM bicarbonate ions; (e) the $pCO_2$ sensor of Example 8 with 10.0 mM bicarbonate ions; and (f) the $pCO_2$ sensor of Example 9 with 15.0 mM bicarbonate ions.
Figure 6B:
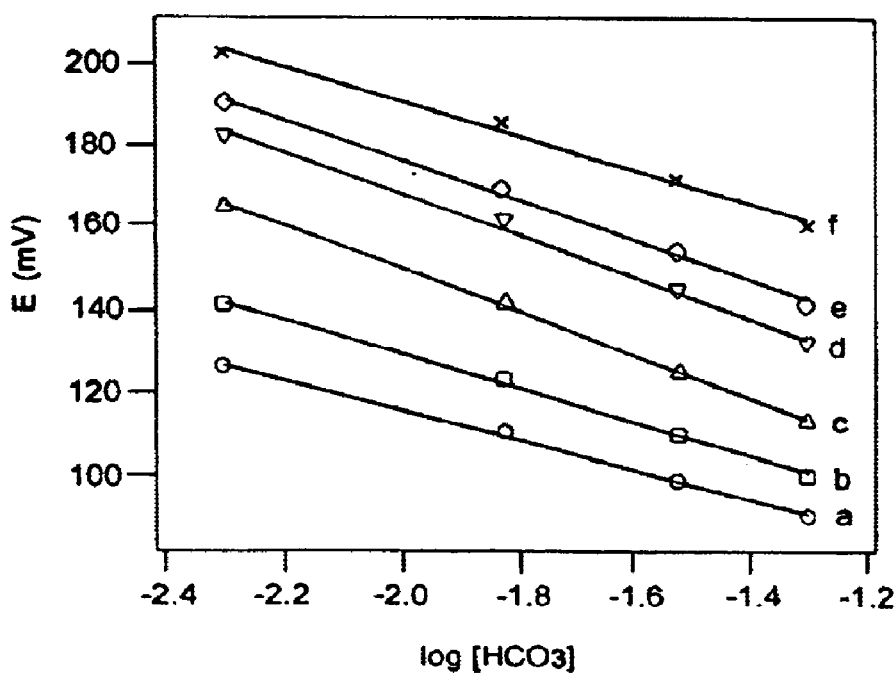
FIG. 6b is calibration curves for the plots of FIG. 6a showing the sensitivity for carbon dioxide.

When the bicarbonate ions are present at levels of as low as 0.5 mM (a) and 2.0 mM (b), as shown in FIGS. 6a and 6b, the carbon dioxide gas sensors respond very quickly, but significantly deteriorated in slope. On the other hand, at bicarbonate ion levels of 5.0 mM (c), 7.0 mM (d) and 10.0 mM (e), the carbon dioxide gas sensors showed high slope with somewhat prolonged response time. Accordingly, when account is taken of slope, the bicarbonate ion level is preferably set to be more than 2 mM.

EXPERIMENTAL EXAMPLE 4

Measurement of Lifetime of Microchip-Based Differential-Type Carbon Dioxide Gas Sensor While being stored in a 5 mM $NaHCO_3$ solution, the carbon dioxide sensor of Example 10, which employed the pH-sensitive gas-permeable membrane of Preparation Example 5 to which N-[3-(trimethoxysilyl)propyl]ethylene diamine was added with the aim of maintaining electrochemical properties of the membrane and improving its adhesiveness, was used to measure total dissolved carbon dioxide levels in the solution. The slope measured was recorded with regard to time. The results are given in FIG. 7.

Figure 7:
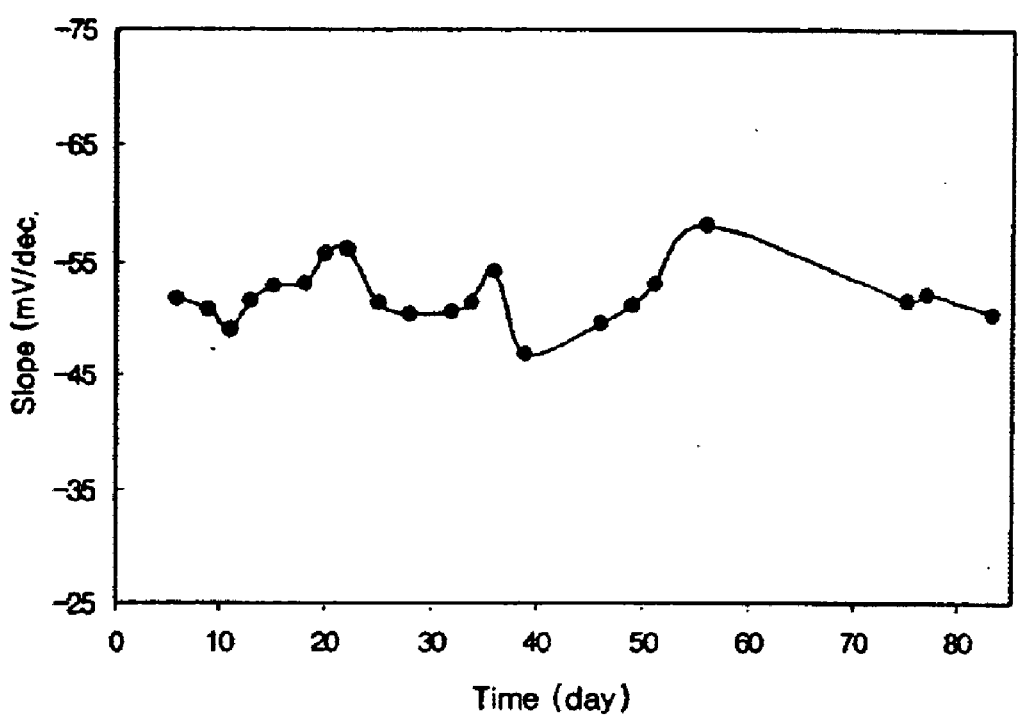
FIG. 7 is a plot showing the lifetime of the $pCO_2$ sensor of Example 1, in which its sensitivity is plotted with response slope to to time (days).

This carbon dioxide gas sensor, which showed the best sensitivity among the microchip-based differential-type carbon dioxide gas sensors of the present invention, as shown in FIG. 7, was found to maintain a slope of at least −50 mV/dec. for 80 days. This period of time was much longer than the lifetime of conventional sensors.

EXPERIMENTAL EXAMPLE 5

Measurement of Partial Carbon Dioxide Pressure in Unknown Solution

The carbon dioxide gas sensor prepared in Example 1, which showed excellent sensitivity, was used to measure the carbon dioxide level of an unknown sample solution and its accuracy was assayed.

Figure 8A:
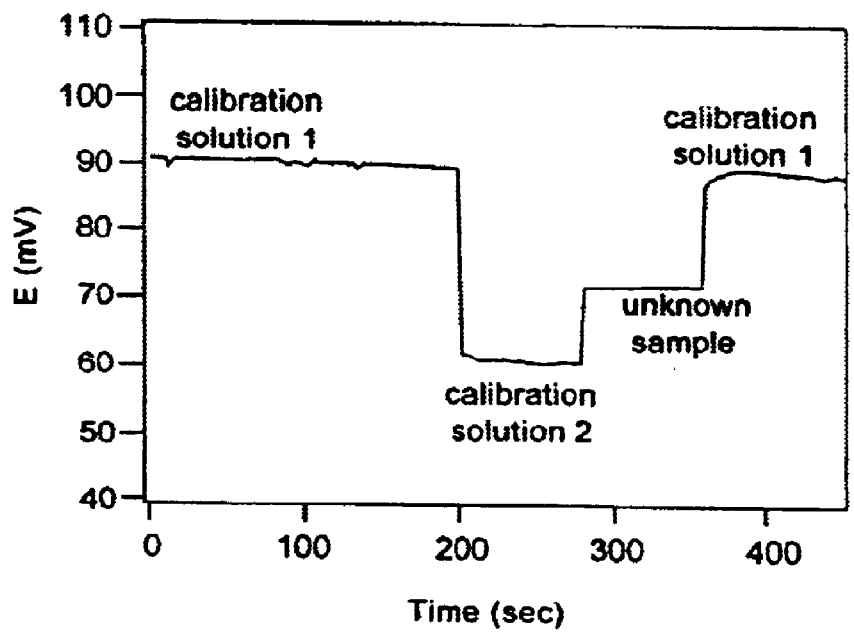
FIG. 8a is a graph in which the potential detected by the $pCO_2$ sensor of Example 1 are plotted with regard to the dissolved carbon dioxide levels of samples.
Figure 8B:
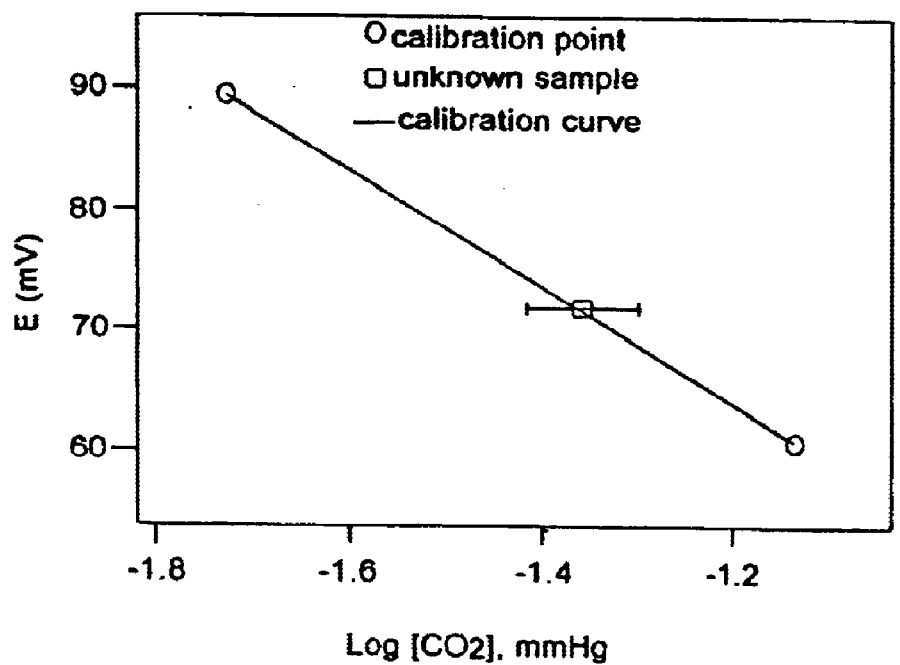

Calibration solution 1 and calibration solution 2, whose compositions are shown in Table 5, below, were determined as for their electric potentials by use of the carbon dioxide gas sensor, as shown in FIG. 8a. Based on the electric potentials measured, a calibration curve was obtained through a flow injection method, as shown in FIG. 8b. Using this calibration curve, an unknown solution was measured to have a partial carbon dioxide pressure of 43.6 mmHg. Meanwhile, the partial carbon dioxide pressure of the same unknown solution was found to be 45.3 mmHg as measured by commercially available blood gas analysis equipment, Nova Biomedical Stat Profile M, which is extensively used in hospitals. Similarity between the two measured partial carbon dioxide pressures may be taken as a proof that the microchip-based differential-type carbon dioxide sensor of the present invention is reliable. Furthermore, the differential-type carbon dioxide gas sensor of the present invention can respond within a shorter period of time than conventional sensors. In addition, it can be easily fabricated, enjoying the advantage of being economically favorable.

TABLE 5

Compositions of Calibration Solutions

| Composition | Content | |
|---|---|---|
| | Calibration Solution 1 | Calibration solution 2 |
| pH (-log [$H^+$]) | 7.60 | 80 |
| $pCO_2$ (mmHg) | 19 | 74 |
| $pO_2$ (mmHg) | 153 | 70 |
| $Na^+$(mM) | 157 | 117 |
| $K^+$(mN) | 6.7 | 2.7 |
| $Cl^-$(Mm) | 124 | 80 |

As described hereinbefore, the microchip-based differential-type carbon dioxide gas sensor of the present invention employs as an inner standard solution for a working electrode an unbuffered hydrogel membrane into which carbonic anhydrase is introduced, so that the time period that it takes to complete the hydration of carbon dioxide can be reduced, thereby measuring the concentrations of carbon dioxide dissolved in sample solutions within a shorter period of time. Additionally, the microchip-based differential-type carbon dioxide gas sensor can be fabricated in small sizes because all their parts, including electrolyte layers, are introduced as dried layer. In the layered structure of the present invention, the sensing part responsible for detecting a species of interest can be formed in such a small size that quantitative analysis for carbon dioxide can be achieved with a very small quantity (1~2 ml) of a sample. Thus, the sensor can find applications in multi component blood analysis and clinical sample analysis. Moreover, such a layered structure enables the development of multi-sensors that are able to detect various ion and gas species on a single chip, as well as being advantageous in mass production, thereby significantly reducing the production cost.

What is claimed is:

1. A microchip-based differential-type carbon dioxide gas sensor, comprising:
   a) at least one working electrode composed of an electrode layer, an unbuffered hydrogel and a pH-sensitive gas-permeable membrane, wherein carbonic anhydrase is incorporated into the unbuffered hydrogel; and,
   b) a reference electrode composed of an electrode layer, an buffered hydrogel and a pH-sensitive gas-permeable membrane.

2. The microchip-based differential-type carbon dioxide gas sensor, as set forth in claim 1, comprising:
   a) a substrate;
   b) multiple electrodes arranged on the substrate, wherein one of the multiple electrodes is the reference electrode and the other multiple electrodes are working electrodes;
   c) an insulating film for separating the multiple electrodes deposited over the substrate, except for the areas for the electrode sites;
   d) pH-sensitive gas-permeable membranes, located atop each of the multiple electrodes;
   e) wherein each of the working electrodes has an unbuffered hydrogel membrane containing carbonic anhydrase located between the working electrode layers and each of the pH-sensitive gas-permeable membranes; and
   f) wherein the reference electrode has a buffered hydrogel membrane located between the reference electrode layer and the pH-sensitive gas-permeable membrane.

3. The microchip-based differential-type carbon dioxide gas sensor as set forth in claim 2, wherein the substrate is selected from the group of alumina, ceramic, silicon, and plastic material.

4. The microchip-based differential-type carbon dioxide gas sensor as set forth in claim 2, wherein the unbuffered hydrogel membrane is composed of a hydrogel comprising $2.4 \times 10^{-2}$~$8.1 \times 10^{-2}$% by weight of sodium bicarbonate, $5.6 \times 10^{-4}$~$5.6 \times 10^{-3}$% by weight of sodium chloride or potassium chloride and 1~4% by weight of a hydroscopic material, and carbonic anhydrase in an amount of 0.1~6.0 mg per ml of the hydrogel.

5. The microchip-based differential-type carbon dioxide gas sensor as set forth in claim 4, wherein the hygroscopic material is selected from hydroxyethyl cellulose, poly(vinyl alcohol), Methocel, (hydroxypropyl)methyl cellulose, polyacrylic acid, polyvinylpyrrolidone, poly (methylmethacrylate), agar and gelatin.

6. The microchip-based differential-type carbon dioxide gas sensor as set forth in claim 2, wherein the buffered hydrogel membrane is prepared from a solution of 1~5 mM sodium chloride or potassium chloride and 1~4% by weight of an hygroscopic material in an acidic buffer.

7. The microchip-based differential-type carbon dioxide gas sensor as set forth in claim 2, wherein the pH-sensitive gas-permeable membrane comprises 32~45% by weight of a polymer matrix, 1.0~45% by weight of a hydrogen ion-selective material, 50~66% by weight of a plasticizer, and 0.9~1.5% by weight of a lipophilic additive.

8. The microchip-based differential-type carbon dioxide gas sensor as set forth in claim 7, wherein the polymer matrix is formed of a material selected from the group consisting of PVC (poly(vinyl chloride)), PU (polyurethane), silicon rubber, and a combination thereof.

9. The microchip-based differential-type carbon dioxide gas sensor as set forth in claim 7, wherein the hydrogen ion-selective material is selected from the group consisting of TDDA (tridodecyl amine), 4-nonadecylpyridine, N,N-dioctadecylmethylamine, and octadecyl isonicotinate.

10. The microchip-based differential-type carbon dioxide gas sensor as set forth in claim 7, wherein the plasticizer is DOS (bis(2-ethylhexyl)sebacate) or NPOE (2-nitrophenyl octyl ether).

11. The microchip-based differential-type carbon dioxide gas sensor as set forth in claim 7, wherein the lipophilic additive is KTpClPB (potassium tetrakis [4-chlorophenyl] borate).

12. The microchip-based differential-type carbon dioxide gas sensor as set forth in claim 7, wherein the pH-sensitive gas permeable membranes further comprises N-[3-trimethoxysilyl)propyl]ethylene diamine.

* * * * *